United States Patent [19]

Hackman et al.

[11] 4,329,511
[45] May 11, 1982

[54] HYDROFORMYLATION PROCESS IMPROVED BY CHOICE OF REACTION SOLVENT AND CONTROL OF PRODUCT STRIPPING PARAMETERS

[75] Inventors: Edward B. Hackman, Corpus Christi; Larry D. Zeagler, Pampa; James S. McLaughlin, Corpus Christi; Carl M. Peabody, Louisville, all of Tex.

[73] Assignee: Celanese Corporation, New York, N.Y.

[21] Appl. No.: 161,827

[22] Filed: Jun. 23, 1980

Related U.S. Application Data

[63] Continuation of Ser. No. 49,998, Jun. 18, 1979, abandoned.

[51] Int. Cl.$^3$ .................... C07C 45/50; C07C 47/02
[52] U.S. Cl. .................... 568/454; 568/909; 252/431 P
[58] Field of Search .............. 568/451, 454, 909, 882; 252/431 P

[56] References Cited

U.S. PATENT DOCUMENTS

| | | | |
|---|---|---|---|
| 3,455,091 | 7/1969 | Herber et al. | 568/451 |
| 4,138,420 | 2/1979 | Unruh et al. | 568/454 |
| 4,139,565 | 2/1979 | Unruh et al. | 568/454 |
| 4,148,830 | 4/1979 | Pruett et al. | 568/454 |
| 4,151,209 | 4/1979 | Paul et al. | 568/451 |
| 4,152,344 | 5/1979 | Unruh | 568/454 |
| 4,158,020 | 6/1979 | Stautzenberger et al. | 568/454 |
| 4,159,999 | 7/1979 | Stautzenberger et al. | 568/454 |
| 4,166,773 | 9/1979 | Higley et al. | 568/451 |

Primary Examiner—Werren B. Lone
Attorney, Agent, or Firm—Ralph M. Pritchett

[57] ABSTRACT

In hydroformylating an olefinic compound to produce an aldehyde derivative thereof employing as catalyst a complex of a Group VIII metal and an organic ligand dissolved in an inert liquid reaction solvent with the aldehyde product being continuously stripped out of the solvent, stripping is facilitated while by-product formation is kept at a minimum by using a solvent of specially-chosen high molecular weight while also controlling the degree of stripping as desired to maintain in the reaction medium a controlled molar concentration of the aldehyde hydroformylation product.

11 Claims, No Drawings

HYDROFORMYLATION PROCESS IMPROVED BY CHOICE OF REACTION SOLVENT AND CONTROL OF PRODUCT STRIPPING PARAMETERS

This is a continuation of application Ser. No. 049,998, filed June 18, 1979, now abandoned.

BACKGROUND OF THE INVENTION

Processes for hydroformylating an olefin to prepare a carbonyl derivative containing one carbon atom more than the parent olefin by reacting the olefin with synthesis gas in the presence of a Group VIII metal, e.g. rhodium, in complex combination with an organic ligand, carbon monoxide also being a component of the catalyst complex, are well known in the art and of growing industrial importance. This technology is summarized, for example, in U.S. Pat. No. 3,527,809 to Pruett et al. The olefin reactant is contacted with the catalyst and the synthesis gas (a mixture of carbon monoxide and hydrogen) in the presence of a liquid reaction medium, which may or may not comprise a separate inert liquid solvent species. A gas comprising the carbon monoxide and hydrogen is typically bubbled through the liquid reaction medium which is contained in a hydroformylation reactor which can be mechanically stirred or which may be agitated solely by the action of reactant gas being bubbled therethrough. The gas, in addition to hydrogen and carbon monoxide, may also contain vapors of the reactant olefin, in a proportion which will depend upon such factors as reaction conversion rate and the volatility of the olefin.

The aldehyde hydroformylation product can be recovered from the liquid hydroformylation reaction medium in various ways, but, especially when the aldehyde is of comparatively low molecular weight, e.g., when it contains from three to about seven carbon atoms and especially when it contains from three to about five carbon atoms, it is conveniently stripped out in vapor form by distillation, evaporation, or, especially, by being stripped out of the hydroformylation reaction zone in the gases which are being bubbled through the liquid contained therein. Hershman et al. have described this technology in "I & EC Product Research and Development" 8, pp 372–375 (1969) in a discussion of the hydroformylation of propylene in a gas-sparged reactor.

In more recent years various patents and other publications have appeared directed to the use of special reaction solvents and/or special techniques for stripping the aldehyde product out of the liquid reaction medium. For example, U.S. Pat. No. 4,148,830 (Pruett et al.) recommends using high-boiling reaction by-products as the reaction solvent, with the aldehyde product being subsequently recovered from the reaction medium in a separate vaporization operation.

The employment of intensive stripping of the liquid reaction mixture not only to recover the aldehyde product but also to reduce the formation of high-boiling reaction by-products is taught in U.S. Pat. No. 4,151,209 to Paul et al., such intensive stripping serving not only to recover the product but also to reduce catalyst deactivation. The stripping can be accomplished by distillation, simple evaporation, or, especially, by the stripping action of the reaction gases being sparged through the liquid contained in the hydroformylation reactor. Any of a number of inert reaction solvents can be employed if desired, including in particular polyalkylene glycols of molecular weight of at least about 500, although the invention itself lies fundamentally in the degree of stripping which is employed and not in choice of the solvent. As the primary control for the degree of stripping, Paul et al. employ the ratio of phosphorus contained in high-boiling reaction by-products to the phosphorus contained in the ligand which is present (the reaction system with which the patentees are concerned being one which employs triorganophosphine ligand). Paul et al. supply no teachings regarding control of stripping when the ligand employed is other than a triorganophosphine, and, so long as the specified high stripping rate is employed, they are not concerned with the identity of any separately-added solvent species which may be added to the reaction system so long as it is chemically inert in the system, compatible with the reactants and catalysts, and sufficiently non-volatile that it will not be removed overhead to any great extent during the stripping operation.

There are additional factors affecting the maintenance of optimum conditions in the stripping operation. Specifically and for example overly-intensive stripping can lead to a condition in which, depending in part upon the proportions of the hydroformylation reaction vessel, the contained liquid reaction medium becomes so expanded with gas bubbles that it begins to be entrained out the top of the reactor with the exiting gases. There is also continuing need for reliable means for reducing where possible the energy requirements and the gas-handling apparatus requirements of the reaction systems as taught in the prior art and as exemplified by Paul et al.

It will also be seen that the control system of Paul et al. is essentially directed to reaction systems where phosphorus-containing ligands are employed. That is, Paul et al. teach a process control system which relies on monitoring the relative concentrations of certain phosphorus derivatives in the liquid reaction medium with the result that in nonphosphorus ligand systems it would be necessary to seek other control parameters or, at best, rely on analogies between the chemistry of organic compounds of phosphorus and those of, for example, antimony.

It is, accordingly, an object of the present invention to provide a more precise and efficient reaction control method for hydroformylation reaction systems as discussed hereinabove. It is a further object to provide a method whereby the degree of reaction product stripping can be reliably controlled without suffering the cost drawbacks of possible over-stripping and the occasional difficulties with reaction liquid entrainment sometimes experienced in the prior art processes. Other objects will be apparent from the following detailed description.

SUMMARY OF THE INVENTION

In accordance with the present invention the stripping employed in recovering the aldehyde product from the liquid reaction mixture formed by the hydroformylation of an alpha-ethylenically unsaturated compound with a Group VIII metal catalyst in complex combination with an organic ligand dissolved in a liquid reaction medium is facilitated, while maintaining minimal formation of undesired high-boiling reaction by-products, by incorporating into the reaction medium an inert solvent which is of relatively high molecular weight as will be further explained below. The molecular weight of the added inert liquid, and the proportion of said inert liquid which is employed, are so chosen that, when the stripping rate is set at such a level that the liquid reaction product mixture being stripped contains about 1 to 2 gram moles of hydroformylation product aldehyde per liter, the mole fraction of product aldehyde in the reaction product mixture will be about 0.4 to 0.7. The crux of the invention lies to a great extent in using a high molecular weight inert liquid in substantial proportions whereby, at a given (and relatively low) molar concentration of product aldehyde in the mixture, its mole fraction in the mixture will, at the same time, be relatively high because of the fact that even a large weight proportion of the high molecular weight solvent will contribute to the mixture only a very few moles. That is, addition of the high molecular weight solvent has reduced the molar density of the mixture, i.e. the total moles of all components contained in a unit volume of the liquid. Thus, the ease of stripping out product aldehyde is greater from a mixture of low molar density comprising substantial quantities of the high molecular weight solvent than would be the case if the solvent were a lower molecular weight material present in the same weight proportion and therefore causing a relatively high molar density in the mixture. Hydroformylation reaction by-products such as condensation derivatives of the aldehyde are also stripped out more easily by reason of the same considerations of enhanced mole fraction obtaining in the presence of the low molar density mixtures as compared with the higher molar density mixtures. While a very low volatility is also desired in the added inert solvent, as already known in the prior art, a high molecular weight is also required in the present invention, and solvents having low volatility but at the same time relatively low molecular weight are not sufficient for the present purposes.

The net result of operating in this manner is that at, for example, a given fixed rate of stripping gas or a given rate of boilup in a stripping-type distillation, it is easier to maintain a specified low molar concentration of aldehyde product in the reaction medium than when the reaction medium is of a relatively lower molecular weight. The relatively low molar concentration of product aldehyde which is easily maintained by the present method also results in reduced formation of undesired condensation products formed from the aldehyde in the reaction medium.

DETAILED DESCRIPTION AND PREFERRED EMBODIMENTS

The present process improvement is directed to liquid-phase catalytic hydroformylation processes broadly, and it will be seen that the details of the particular reaction system being dealt with are secondary. That is, the controlling parameters comprise predominantly vapor pressure, solubility, and molecular weight of the several system components rather than their chemical composition. The method is broadly applicable to any hydroformylation system in which the aldehyde product is to be separated as a vapor from the liquid reaction medium in which it has been formed. The invention does not lie in the discovery of any new hydroformylation reaction system insofar as the chemistry of such systems is concerned, but only in an improved method for removing volatile reaction products rapidly and efficiently from the reaction product mixture while inhibiting by-product formation. However, the following is a summary of the hydroformylation technology the operability of which is enhanced by application of the present process improvement:

Group VIII metals broadly, particularly rhodium and ruthenium and especially rhodium, are employed in organometallic complexes as catalysts for the reaction of a synthesis gas (i.e., a mixture of hydrogen and carbon monoxide) with alpha-olefins to form aldehyde derivatives of the olefins which have one more carbon atom than the parent olefin. While a wide range of olefinic feedstocks can be employed in such processes, including substituted olefins and especially olefins having no heteroatoms other than oxygen, olefinic feedstocks of industrial importance comprise predominantly alpha-olefinic hydrocarbons of 2 to about 20 carbon atoms, especially 2 to about 8 carbon atoms. While the present process improvement is broadly applicable to the hydroformylation of olefins of 2 to about 20 carbon atoms, considerations of vapor pressure at the temperatures normally employed in hydroformylation reaction systems mean that, as will be explained hereinbelow, its most useful applications are with olefins, and especially olefinic hydrocarbons, of 2 to about 6 carbon atoms. Particular utility obtains in processes for hydroformylating ethylene and propylene. These known hydroformylation processes are carried out at superatmospheric pressure, typically under a partial pressure of about 4 to 20 atmospheres of hydrogen and carbon monoxide combined and with the molar ratio of hydrogen to carbon monoxide being about 0.5:1 to 10:1. The hydroformylation reaction temperature is normally within the range of 80° C. to 150° C. It will be understood that the hydroformylation reaction parameters are explained here by way of general background and not as limitations on the present process improvement, which does not have to do directly with the hydroformylation reaction itself.

The liquid reaction medium or catalyst solution which is employed comprises, as is already known in the art, (a) the catalyst complex, (b) typically, an excess of the organic ligand employed in forming the complex over and above the amount required to complex the metallic component of the catalyst, (c) the hydroformylation reaction product along with by-products typically resulting from undesired condensation of the hydroformylation product aldehyde with itself, (d) a quantity of the olefin being hydroformylated, in an amount varying with the molecular weight of said olefin (the proportion of liquid olefin in the reaction medium usually being greater with high molecular weight olefins than with lower alkenes such as ethylene), and (e) in most systems involving the processing of olefins of low to moderate molecular weight, an inert reaction solvent. With higher weight olefins such as, for example, octene, the olefin itself in liquid phase can function as reaction solvent.

The catalyst contained in the reaction mixture can be, as known in the art, any Group VIII metal complexed with an organic ligand. It will be understood that, while the complex is characterized as comprising the metal and the organic ligand, the active catalyst as it actually functions in the reaction is a hydridocarbonyl. That is, the catalytic metal is complexed with hydrogen and carbon monoxide as well as with an organic ligand. While other organic ligands can be employed, those of particular significance comprise either monodentate or polydentate triorganophosphines, triorganophosphites, triorganoarsines, or triorganostibines, with the phosphines and phosphites being of particular industrial importance. Simple monodentate phosphines and phosphites, as exemplified by triphenylphosphine and triphenylphosphite, are commonly employed industrially. However, polydentate ligands have advantages in that large excesses of ligand which are often used with the monodentate ligands are not needed. For example, the phosphine-modified ferrocene-based ligands as taught in U.S. Pat. No. 4,138,420 to Unruh et al., are applicable as well as the sterically restricted bidentate phosphorus-containing ligands described in U.S. Pat. No. 4,139,565. Ligands modified by the incorporation of electronegative substituents into the molecule also have advantages, as set forth in U.S. Pat. No. 4,152,344 to Unruh. The catalytic complex can be formed in situ in the hydroformylation reactor, or it can be preformed, the exact nature and origin of the hydroformylation catalyst being outside the scope of the present invention. It should be mentioned, as prior art which is slightly relevant to the present invention, that one mode of introducing catalyst into the reaction system can, if desired, entail the employment, as a solvent in which the catalyst is introduced into the reaction system, of relatively low molecular weight polyalkylene glycols, as disclosed in copending U.S. application Ser. No. 828,123 U.S. Pat. Nos. 4,158,020 and 4,159,999 filed Aug. 26, 1977, by Stautzenberger et al. The relevance of these low weight polyalkylene glycols to the present invention is that they are similar chemically to the polyalkylene glycols which, as will be explained hereinbelow, are especially applicable as reaction solvents in the present process improvement. The polyglycols of Stautzenberger et al. are extremely compatible with the polyalkylene glycol reaction solvents of the present invention, but they are much lower in molecular weight such that their use as solvent for introducing the catalyst into the reaction system would not inherently achieve the objects of the present process improvement which requires higher molecular weights.

The concentration of catalyst to be maintained in the hydroformylation reaction medium is not critical to the successful employment of the present invention. Typically, however, when the catalytic metal is rhodium and when the ligand is triphenylphosphine, the liquid reaction medium will contain about 0.01 to 1.0% rhodium and up to about 20% or more triphenylphosphine by weight where suppression of iso-aldehydes is desired. In hydroformylating ethylene, the iso-aldehyde problem does not exist, and very low ligand concentrations can be employed, e.g. 1% or less. In the absence of the added inert reaction solvent with which the present invention is concerned, the triphenylphosphine content in hydroformylating propylene, for example, may be as high as about 40%. Typically, the ligand concentration will not exceed about 45 weight percent.

The identity of the inert solvent which is sometimes used in the reaction system as taught by the prior art is not critical so long as it be miscible with the catalyst system and with the reactants and reaction products, low in volatility so as to facilitate stripping reaction product and by-products from it, and, of course, either chemically inert in the hydroformylation reaction system or else forming in that system a derivative which is itself inert while still fulfilling the other named requirements. (That is, a suitable solvent could be one which might undergo hydrogenation in the reactor and then in the hydrogenated form, be inert to further reaction.) Molecular weight is not a significant factor in the reaction solvents as taught in the prior art except as it relates to volatility, relatively high molecular weight being desired, of course, to facilitate retention of the inert solvent as a heavy end while the reaction products are stripped out of it. Thus, in the prior art as exemplified by U.S. Pat. No. 4,151,209, it is already known to employ any of a large number of inert liquids including, for example, alkyl-substituted benzenes; pyridine and alkyl-substituted pyridines; tertiary amines; high-boiling esters such as dialkyldicarboxylates and triorganophosphates as well as esters of polyols such as trimethylolpropane and pentaerythritol; ketones; alcohols such as the butanols; nitriles such as acetonitriles; and hydrocarbons including both saturated hydrocarbons such as kerosene, mineral oil, cyclohexane, naphtha, etc. and aromatics such as biphenyl. It is further emphasized in U.S. Pat. No. 4,151,209 that, in addition to the prior art solvents as just listed, the high degree of stripping taught by the patentees makes it desirable to employ solvents which are of extremely low volatility, in particular compounds or mixtures of compounds which are less volatile than the ligands used in the hydroformylation reaction many of which are themselves of very low volatility. Thus, it is taught in U.S. Pat. No. 4,151,209 that particularly useful solvents include triphenylphosphine oxide and polyglycols, e.g. polyethylene glycol and polypropylene glycol, which have molecular weights of at least about 500. The teachings of the patentees are that molecular weight of the polyalkylene solvents is important as a factor relating to volatility, with molecular weight in and of itself not otherwise being significant.

As mentioned previously, it is also known to use as solvent some or all of the high-boiling aldehyde condensation products which are formed as by-products in the course of the hydroformylation reaction, as taught in U.S. Pat. No. 4,148,830 to Pruett et al.

In practicing the present invention it is possible to use a solvent of any of the types just listed, except that molecular weight in and of itself is a significant factor in addition to low volatility. That is, it is desired that the solvent have a molecular weight of at least about 700 (or higher in some circumstances as will be explained) even though solvent volatility, if this were the only factor being considered, might be sufficiently low at lower molecular weights to satisfy the requirements of the prior art as exemplified by U.S. Pat. No. 4,151,209. Subject to this requirement regarding solvent molecular weight, the solvent can, insofar as its chemical characteristics are concerned, be of any of the types already listed hereinabove. Especially useful solvents, however, which fit all the criteria just set forth and which are also available industrially in a wide range of molecular weights, are the polyalkylene glycols, especially—because of their ready availability—polyethylene glycol and polypropylene glycol. In this context, the term "polyalkylene glycol" refers both to polyalkylene glycols as such (that is, to polymeric alkylene glycols having a hydroxy group at each end) and also to those having one or both ends capped with an alkoxy group such as butoxy. In addition to being readily available in a wide range of molecular weights, these materials are suitably inert and also compatible with the several components of the hydroformylation system.

In carrying out the present improved process the hydroformylation reaction is conducted in the same manner as in any of the several variants of those prior-art processes which do employ an added inert solvent. Mechanical agitation of the liquid contents of the hydroformylation reactor can be employed if desired, but it is simple and satisfactory to obtain adequate agitation by sparging the synthesis gas through the liquid reaction medium. A mixture of gases and vapors withdrawn from the top of the reaction vessel contains the aldehyde product in vapor form, as well as unreacted olefin. The aldehyde is recovered from these withdrawn gases and vapors, which are then recycled to the reaction sparger along with fresh olefin and synthesis gas. The reaction temperature and pressure are set at known prior-art levels at which the hydroformylation reaction takes place at commercially satisfactory rates and yields. The rate of gas recycle can be varied to control the rate at which product is stripped out of the liquid reaction mixture contained in the reaction vessel. It will be seen, of course, that stripping rate is affected by all three factors (temperature, pressure, and gas recycle rate) and that it is possible, as already understood in the prior art, to vary each of these factors to some extent to attain a desired product stripping rate.

An alternative mode of operation which can be employed in place of the above-described method for stripping product out of the reactor with the recycling gases is to withdraw a slip stream of liquid from the hydroformylation reactor and distill it to recover a distillate comprising the aldehyde product while leaving a distillation residue comprising the reaction solvent and catalyst, this residue then being returned to the hydroformylation reactor. Yet another alternative is to subject the withdrawn slip stream to simple evaporation, although distillation is preferable because it facilitates making a sharper separation between reaction products and high-boiling solvent.

As previously explained, conducting the reaction and the product recovery operation in accordance with the prior art methods has entailed the considerations of volatility, chemical compatibility, and product degradation through intermolecular condensation reactions (as emphasized, for example, in U.S. Pat. No. 4,151,209). All these factors continue to be significant in the present improved process, of course, but it has now been realized that yet another parameter is of industrial significance in carrying out the product recovery at minimal cost and at optimal efficiency in, for example, the required rate of gas circulation necessary to recover the volatile products and simultaneously prevent buildup of the heavier reaction by-products. This additional parameter is the mole fraction of aldehyde in the liquid reaction medium contained in the hydroformylation reactor and, associated with the mole fraction, the molar concentration of product aldehyde in the liquid. If a low volatility is the only consideration in choosing the inert reaction solvent which is to be employed, all that would be required in adjusting the composition of the liquid reaction mixture from which the aldehyde product is being stripped would be that the solvent be chemically inert, that it be compatible with the other components of the system, and that it be present in sufficient quantity to maintain fluidity. With such a system it is possible to maintain operability and achieve, for example, the purposes of U.S. Pat. No. 4,151,209 in maintaining catalyst activity. However, stringent stripping conditions may be required to accomplish these ends with prior-art solvents. Alternatively, with less stringent stripping while using the prior-art solvents, one may approach the borderline of conditions under which a buildup of high-boiling reaction by-products begins to take place.

In accordance with the present process improvement, the ease of stripping is improved as compared with the prior art by employing as the inert solvent a liquid which has a higher molecular weight than previously contemplated, without necessarily changing, for example, the molar proportion of the solvent to the other components. Essentially, substitution of a solvent having a high molecular weight in place of a solvent (or other system component) which has a relatively lower molecular weight brings about a reduction in the molar density of the mixture, i.e., the total moles of all components of whatever nature which are present in a unit volume of the liquid. The result of this modification is that, at a constant molar concentration of aldehyde in the mixture, the mole fraction of aldehyde is greater in the case of the modified mixture having the lowered molar density than it is with the unmodified mixture wherein, lacking the high molecular weight solvent additive, the molar density is higher. Alternatively and preferably, to maintain a given mole fraction of aldehyde in the modified mixture containing the high molecular weight solvent requires a lower aldehyde concentration (expressed in, for example, moles per liter) than is required to maintain the same aldehyde mole fraction in the unmodified mixture. Thus one can, as he wishes, either reduce the rate of stripping gas or else, with the rate of stripping gas being unchanged, enhance the efficiency of aldehyde stripping per unit quantity of stripping gas. Since the formation of undesired condensation derivatives of the product aldehyde is a function of the concentration of that aldehyde in the reaction product mixture, the present technique facilitates reducing such side reactions or almost eliminating them entirely. Particularly satisfactory results obtain when the mole fraction of product aldehyde in the liquid reaction mixture is from about 0.4 to about 0.7.

To effect the desired reduction in molar density, it is recommended that sufficient high molecular weight diluent be incorporated into the hydroformylation reaction medium that the resulting liquid mixture contain at least about 50% of the high molecular weight diluent, computed on the product aldehyde-free basis. Lesser proportions of the diluent will have some effect, of course, but a proportion of at least 50% by weight is desirable. Proportions higher than about 50 weight percent are desirable, up to an upper limit which will be imposed by the fact that in many reaction systems there will be a substantial excess of ligand, e.g. triphenylphine, which will itself constitute a substantial fraction of the reaction medium. For example, the liquid may frequently contain about 30-40 wt % of excess ligand which is thus unavoidably a substantial component. Broadly speaking, then, it is recommended that the diluent be incorporated into the reaction medium in a proportion of at least about 50% by weight, with lower proportions of the order of about 40% by weight or even less still being advantageous, while the upper limit is normally imposed by the fact that there are present other essential components such as the organic ligand which can be reduced in concentration only at the cost of reduced reactor throughput. In most situations the diluted reaction medium will contain, by weight, about 40% to about 60%, or more broadly about 40% to 95% of the high molecular weight diluent on the product aldehyde-free basis. Product aldehyde itself will typically amount to roughly 10% to 15% of the total reaction mixture.

When the olefin being hydroformylated is ethylene, it is recommended that the added diluent have a molecular weight of about 700 to 800. When the reactant olefin is propylene or a higher olefin, it is preferred that the diluent have a molecular weight of about 1500 to 2000. With further reference to the matter of the molecular weight of the diluent, it will be understood that some of the prior-art reaction solvents may themselves have a high molecular weight although it may not be appreciated that the hydroformylation system in which they are being used can, with some additional control in the stripping operation, enjoy some of the benefits of the present method. Preferably, however, the inert solvent should have a molecular weight of at least about 700 in order that a given quantity of it may have a significant effect in reducing the molar density of the mixture. As the molecular weight of the diluent increases, it of course becomes more efficacious in the desired reduction of molar density although with increasing molecular weight of the diluent the chemical rate of hydroformylation may be lowered and the mass-transfer properties of the resulting mixture become less satisfactory such that it is desirable in some cases to increase the catalyst concentration and/or increase the quantity of a liquid reaction medium per unit of desired reactor aldehyde output. While there is no sharp upper limit of solvent molecular weight above which the present method is inoperative, it is preferred that the molecular weight of the diluent liquid not exceed about 3000.

In carrying out the hydroformylation reaction using the present diluted reaction medium it is, as previously explained, easier to maintain a relatively low concentration of product aldehyde than when using undiluted reaction medium. Reduction in aldehyde concentration means a reduction in by-product formation. The aldehyde content (i.e., the content of the desired hydroformylation product aldehyde as distinguished from undesired heavy by-products which might also have aldehyde moiety in the molecule) is controlled by controlling the intensity of the product stripping which is employed to remove the aldehyde from the reaction medium. The details of how this control is maintained are, of course, obvious to one skilled in the art. That is, an elevation of stripping temperature or an increase in the rate of stripping gas throughput serves to reduce the product aldehyde content of the reaction product mixture which is being stripped. In practicing the present invention it is recommended that the stripping be so controlled as to maintain in the liquid reaction medium contained in the hydroformylation reactor an aldehyde content of about 1 to 2 gram moles per liter. Very good results obtain when the aldehyde concentration is 1 to 1.5 in the case of propionaldehyde and 1.5 to 2.0 in the case of butyraldehydes. These relatively low aldehyde contents are recommended if it is desired to hold to a minimum the formation of undesired aldehyde condensation reaction by-products. It will be seen, however, that it is also possible within the scope of the invention to use the present dilution method not for reducing by-product formation by stripping to this relatively low aldehyde concentration but, rather, to take advantage of the fact that, at a given and unchanged aldehyde concentration in the reaction mixture, the stripping rate can be reduced with resultant saving in energy and in, for example, stripping gas recirculation apparatus. That is, one can use the improved properties of the present diluted mixture (improved as regards the ease of stripping the aldehyde therefrom) either to strip out the aldehyde more completely without increasing the rate of, for example, stripping gas recirculation or, alternatively, he can allow the aldehyde concentration in the liquid to be unchanged but still benefit from the incorporation of the diluent by economizing through reducing the intensity of the stripping operation.

The following examples are given to illustrate further the application of the invention. It will be understood that many variations can be made therefrom within the scope of the invention.

EXAMPLE 1

Propylene is hydroformylated to produce butyraldehyde by being sparged, in admixture with synthesis gas, through a liquid reaction medium, or catalyst solution, which is contained in a hydroformylation reactor operating at 115° C. and at a pressure of 22.4 atmospheres absolute, and cooled by recirculation of its liquid contents through an external heat exchanger and back into the top of the vessel. The reactor is agitated by the bubbling action of the gas sprager. The gas mixture being sparged into the base of the reactor comprises, in mole percent, 32.68% hydrogen, 13.16% carbon monoxide, 21.79% propylene, 25.25% propane, 5.12% methane, slightly less than 1% butyraldehydes, and lesser quantities of various minor components. The propane and methane are present as a result of having been allowed to build up in the course of recycling gases from the reactor through a product recovery operation and back into the reactor, uncontrolled buildup being prevented by continuously purging a portion of the recycling gas.

The liquid reaction medium, or catalyst solution, contained in the hydroformylation reactor has the following composition.

| BUTYRALDEHYDE PRODUCTION LIQUID REACTION MEDIUM | | | |
|---|---|---|---|
| Component | Mol % | Wt % | gm Mols per Liter of Solution |
| i-Butyraldehyde | 4.55 | 1.31 | 0.164 |
| n-Butyraldehyde | 47.38 | 13.69 | 1.71 |
| Butanols | 1.35 | 0.40 | 0.046 |
| TPP[1] | 33.11 | 34.79 | 1.19 |
| TPPO[2] | 2.69 | 3.00 | 0.097 |
| PDPP[3] | 2.19 | 2.00 | 0.079 |
| Heavy ends | 0.78 | 0.55 | 0.033 |
| Rhodium | 0.63 | 0.26 | 0.023 |
| Polyglycol[4] | 7.32 | 44.0 | 0.209 |
| Total | 100.0 | 100.0 | 3.6 |

[1]Triphenylphosphine
[2]Triphenylphosphine oxide
[3]Propyldiphenylphosphine
[4]Polypropylene glycol capped with butoxy group at one end.

The butyraldehydes content in the reactionmedium is maintained at approximately 1.9 gm mols per liter as tabulated above by controlling the rate at which the gas is sparged into the reaction medium. Under the conditions of pressure, temperature, and reaction medium as tabulated above, the desired butryaldehydes content is maintained by controlling the gas sparge rate at approximately 199 gm mols of gas per hour per liter of liquid reaction medium contained in the hydroformylation reactor and excluding liquid contained in the recirculated cooling loop.

The gas evolving from the surface of the liquid reaction medium passes upwardly through a short section of perforated gas-liquid contacting trays (5 trays) against a small down flowing stream of crude butyraldehyde product amounting to approximately 0.05 to 0.1 grams of this crude butyraldehyde scrubbing liquid per liter of gas evolving from the surface of the liquid reaction medium and entering the perforated tray section. This liquid comprises, by weight, approximately 88% n-butyraldehyde, 7.5% isobutyraldehyde, 2% propane, and 1.5% propylene. From the bottom tray, the scrubbing liquid flows back into the hydroformylation reactor. The product gas leaving the top of the perforated tray section amounts to 183 gram mols of the total gas per hour per liter of liquid contained in the hydroformylation reactor and comprises, in mol %, approximately 30.1% hydrogen, 9.1% carbon monoxide, 5.6% methane, 18.8% propylene, 28.1% propane, 0.6% isobutyraldehyde, 6.5% normal butyraldehyde, and lesser quantities of minor diluents. It also contains approximately 0.5 gram of reaction heavy ends per hour per liter of liquid reaction medium contained in the hydroformylation reactor, or approximately 0.001 mol % in the reactor outlet gas. The gas just described is then cooled to approximately 50° C. without appreciable lowering of its pressure, to form a crude aldehyde product condensate and a recycle gas stream. The bulk of the gas is recycled to the hydroformylation reactor while a portion is vented to control buildup of inerts. The majority of the condensate liquid is drawn off as crude aldehyde product, while a small portion is returned to the top of the perforated tray section as previously explained.

The net make of gases and vapors, i.e. the sum of the crude aldehyde product drawoff, the gas recycle, and the gas vent stream, amounts to 179.5 gram mols per hour per liter of liquid reaction medium of catalyst solution contained in the hydroformylation reactor and contains 55.22 mols of hydrogen, 16.63 mols of carbon monoxide, 33.59 mols of propylene, 50.38 mols of propane, 10.35 mols of normal butyraldehyde, 1.00 mol of isobutyraldehyde, 10.17 mols of methane, 0.14 mol of water, 0.02 mol of butanols, and the remainder minor diluents. The space-time yeild of n-butyraldehyde is 12 to 14 grams mols per liter of liquid reaction medium per hour computed, as above, on the basis of liquid contained in the reactor itself. The concentration of reaction heavy ends does not build up appreciably in the catalyst solution or liquid reaction medium over extended periods of time, i.e., over a period of months, and the activity of the catalyst is also not appreciably decreased over a period of months.

While the process as exemplified here operates at 22.4 atmospheres pressure, lower pressures can be employed down to about 10 atmospheres, below which the reaction rate begins to fall off more than is normally desired. The only upper limit on pressure is imposed by economic considerations of apparatus design strength, although it will be understood that, as pressure increases, the mols of stripping gas required per unit of aldehyde to be stripped out will increase for reasons obvious to those skilled in chemical engineering. Normally pressures will not exceed 70 atmospheres.

EXAMPLE 2

Ethylene is hydroformylated to produce propionaldehyde by being sparged, in admixture with synthesis gas and reaction recycle gas as in Example 1, through a liquid reaction medium contained in a hydroformylation reactor operated at 115° C. and 35 atmospheres absolute and, as in Example 1, cooled by recirculation of the contained liquid through an external heat exchanger and back into the top of the top of the reaction vessel. As in Example 1, the contents of the reactor are agitated by the action of the gas sparger. The gas sparged into the base of the reactor comprises, in mol percent, 60.5% hydrogen, 19.9% carbon monoxide, 10.7% ethylene, 3.0% methane, 0.6% ethane, 0.6% carbon dioxide, 2.0% propionaldehyde, and the remainder minor contaminants. This gas is sparged through the liquid reaction medium, or catalyst solution, at the rate of 177.1 gram mols per hour per liter of catalyst solution in the reactor itself, as in Example 1, and the propionaldehyde stripped out of the catalyst solution with the exiting gases amounts to 20.5 gram mols of propionaldehyde per liter of catalysts solution per hour.

The liquid reaction medium, or catalyst solution, contained in the hydroformylation reactor and through which the gas is sparged as just explained, has the following composition:

| PROPIONALDEHYDE PRODUCTION LIQUID REACTION MEDIUM | | | |
|---|---|---|---|
| Component | Mol % | Wt % | gm Mols per Liter of Solution |
| Propionaldehyde | 53.0 | 8.7 | 1.37 |
| 2-Methylpentanal | 0.07 | 0.02 | 0.0018 |
| Ester MW 174 | 1.4 | 0.7 | 0.0364 |
| Heavy ends | 0.6 | 0.4 | 0.0144 |
| Triphenylphosphine | 0.9 | 0.6 | 0.022 |
| Rhodium | 0.04 | 0.01 | 0.001 |
| Polyglycol[1] | 44.1 | 89.6 | 1.14 |

[1]Polypropylene glycol capped with butoxy group at one end. Molecular weight approximately 725. Sold by Union Carbide Corporation under trade name "UCON LB165".

The gases evolved from the surface of the catalyst solution are drawn out from the top of the hydroformylation reactor and are cooled to 50° C. at 34.67 atmospheres absolute pressure. The condensate is drawn off as crude aldehyde product, and the uncondensed gas is recycled to the hydroformylation reactor. The gases drawn out from the top of the hydroformylation reactor comprise, in mol percent, 63.4% hydrogen, 12.7% carbon monoxide, 14.1% propionaldehyde, 3.7% methane, 3.0% nitrogen, 1.3% ethylene, 0.8% ethane, $2.1 \times 10^{-4}$% methylpentanal, and $2.1 \times 10^{-4}$ ester.

With the reaction system operating in this manner, the space-time yield of propionaldehyde amounts to approximately 16.9 gm mols of propionaldehyde per hour per liter of catalyst solution. The molar density of the catalyst solution including the polyalkylene glycol diluent is 2.6 gm mols per liter. The concentration of reaction heavy ends does not build up appreciably over an extended period of time, and the activity of the catalyst is also stable for extended periods.

While the process as exemplified here operates at 35 atmospheres pressure, lower pressures can be employed down to about 15 atmospheres, below which the reaction rate begins to fall off more than is normally desired. The only upper limit on pressure is imposed by economic considerations of apparatus design strength, although it will also be understood that, as pressure increases, the moles of stripping gas required per unit of aldehyde to be stripped out will increase for reasons obvious to those skilled in chemical engineering. Normally pressures will not exceed 70 atmospheres.

The embodiments of the invention in which an exclusive property or privilege is claimed are defined as follows:

1. In a process for hydroformylating an olefin of 2 to about 20 carbon atoms having an ethylenic double bond in the alpha position by reacting said olefin at about 80° C. to 150° C. and superatmospheric pressure with carbon monoxide and hydrogen in admixture with a liquid reaction medium comprising a high-boiling inert reaction solvent containing an effective amount of a hydroformylation catalyst comprising a Group VIII metal in complex combination with a monodentate or polydentate ligand comprising triorganophosphine, triorganophosphite, triorganoarsine, or triorganostibine moiety to form a liquid reaction product mixture comprising said ligand, an aldehyde derivative of said olefin, and said highboiling inert reaction solvent while continuously stripping said liquid reaction product mixture by distillation, evaporation, or gas stripping to recover vapors comprising said aldehyde therefrom, the improvement which comprises:

(a) employing as said high-boiling inert reaction solvent a liquid which has a molecular weight of at least about 700 and which is a solvent for said catalyst and said olefin, said solvent being incorporated into said liquid reaction medium in a proportion of about 40% to 95% by weight, and (b) controlling the rate of stripping at a level such that, when the olefin is ethylene, the concentration of propionaldehyde maintained in the liquid reaction product mixture is about 1 to 2 gram moles per liter or, when the olefin is propylene or a higher alkene, the maintained concentration of the sum of the corresponding normal and iso-aldehyde hydroformylation derivatives is about 1 to 2 gram moles per liter.

2. The improvement of claim 1 wherein the olefin is a monoalkene of 2 to about 6 carbon atoms and the ligand is a triorganophosphine.

3. The improvement of claim 2 wherein the inert reaction solvent is a polyalkylene glycol.

4. The improvement of claim 3 wherein the polyalkylene glycol is a polypropylene glycol.

5. The improvement of claim 3 further characterized by employing a polyalkylene glycol of molecular weight approximately 700 to 800 when the olefin is ethylene, or a polyalkylene glycol of molecular weight approximately 1500 when the olefin is propylene or a higher alkene.

6. The improvement of claim 5 further characterized by adjusting the stripping rate and the proportion of inert solvent in the reaction medium in conjunction with one another so that, at the desired set molar concentration of aldehyde in the liquid reaction product mixture, the mole fraction of aldehyde in said reaction product mixture will be about 0.4 to 0.7.

7. The improvement of claim 5 wherein the organic ligand is triphenylphosphine.

8. In a process for hydroformylating propylene at about 115° C. and at superatmospheric pressure, which process comprises passing a gas comprising hydrogen, carbon monoxide, and propylene through a liquid reaction medium contained in a hydroformylation reaction zone and containing a catalytically effective amount of a hydroformylation catalyst comprising a complex of rhodium with a triorganophosphine to form a reaction product comprising n-butyraldehyde, said butyraldehyde being continuously removed from said hydroformylation reaction zone by stripping said liquid reaction medium with said gas, the improvement which comprises:

(a) incorporating into said liquid reaction medium a high-boiling inert solvent which is a polypropylene glycol of about 1500 molecular weight in an amount such that the concentration of said polypropylene glycol in said liquid reaction medium is about 40 to 45% by weight, and (b) controlling the stripping rate at a level such that the concentration of butyraldehyde in said liquid reaction medium is maintained about 1.5 to 2.0 gram moles per liter.

9. The improvement of claim 8 wherein the triorganophosphine is triphenylphosphine.

10. In a process for hydroformylating ethylene at about 115° C. and at superatmospheric pressure, which process comprises passing a gas comprising hydrogen, carbon monoxide, and ethylene through a liquid reaction medium contained in a hydroformylation reaction zone and containing a catalytically effective amount of a hydroformylation catalyst comprising a complex of rhodium with a triorganophosphine to form a reaction product comprising propionaldehyde, said propionaldehyde being continuously removed from said hydroformylation reaction zone by stripping said liquid reaction medium with said gas, the improvement which comprises:

(a) incorporating into said liquid reaction medium a high-boiling inert solvent which is a polypropylene glycol of about 700 to 800 molecular weight in an amount such that the concentration of said polypropylene glycol in said liquid reaction medium is about 80% to about 95% by weight on the aldehyde-free basis, and (b) controlling the stripping rate at a level such that the concentration of propionaldehyde in said liquid reaction medium is maintained at about 1.0 to 1.5 gram moles per liter.

11. The improvement of claim 10 wherein the triorganophosphine is triphenylphosphine.

* * * * *

UNITED STATES PATENT AND TRADEMARK OFFICE
CERTIFICATE OF CORRECTION

PATENT NO. : 4,329,511
DATED : May 11, 1982
INVENTOR(S) : Edward B. Hackman, Larry D. Zeagler,
James S. McLaughlin, and Carl M. Peabody It is certified that error appears in the above-identified patent and that said Letters Patent are hereby corrected as shown below:

In column 10, in the last footnote following the table, after "end." insert--Molecular weight approximately 1500. Sold by Union Carbide Corp. under trade name "UCON LB625".--

Signed and Sealed this

Thirty-first Day of August 1982

[SEAL]

Attest:

GERALD J. MOSSINGHOFF

Attesting Officer      Commissioner of Patents and Trademarks